United States Patent [19]  
Fukuda et al.

[11] 4,092,069  
[45] May 30, 1978

[54] SPECTROPHOTOMETER

[75] Inventors: Yoshio Fukuda; Jugoro Suzuki; Toshiaki Fukuma; Michinosuke Takada, all of Kyoto, Japan

[73] Assignee: Shimadzu Seisakusho Ltd., Kyoto, Japan

[21] Appl. No.: 704,530

[22] Filed: July 12, 1976

[30] Foreign Application Priority Data

July 19, 1975 Japan .................... 50-100786

[51] Int. Cl.² .................... G01V 3/42; H01V 39/12
[52] U.S. Cl. .................... 356/88; 250/214 AG; 356/179; 356/205
[58] Field of Search .................... 356/88, 179, 204–206, 356/212; 250/565, 575, 214 AG

[56] References Cited

U.S. PATENT DOCUMENTS 3,623,817  11/1971  Celio .................... 356/179
3,972,617  8/1976  Shibata et al. .................... 356/88

Primary Examiner—John K. Corbin
Assistant Examiner—Wm. H. Punter
Attorney, Agent, or Firm—Fidelman, Wolffe & Waldron

[57] ABSTRACT

A spectrophotometer comprising means for producing electrical signals Er and Es corresponding to reference and measuring beams, respectively; means for multiplying the value Es by a factor $k$ to produce an electrical signal corresponding to the value kEs; means for controlling said signal producing means so as to keep the value (Er + kEs) constant; and means for producing an electrical signal corresponding to the value (Er − kEs), whereby minute changes of the absorbance of a sample can be accurately measured without logarithmic conversion.

22 Claims, 7 Drawing Figures

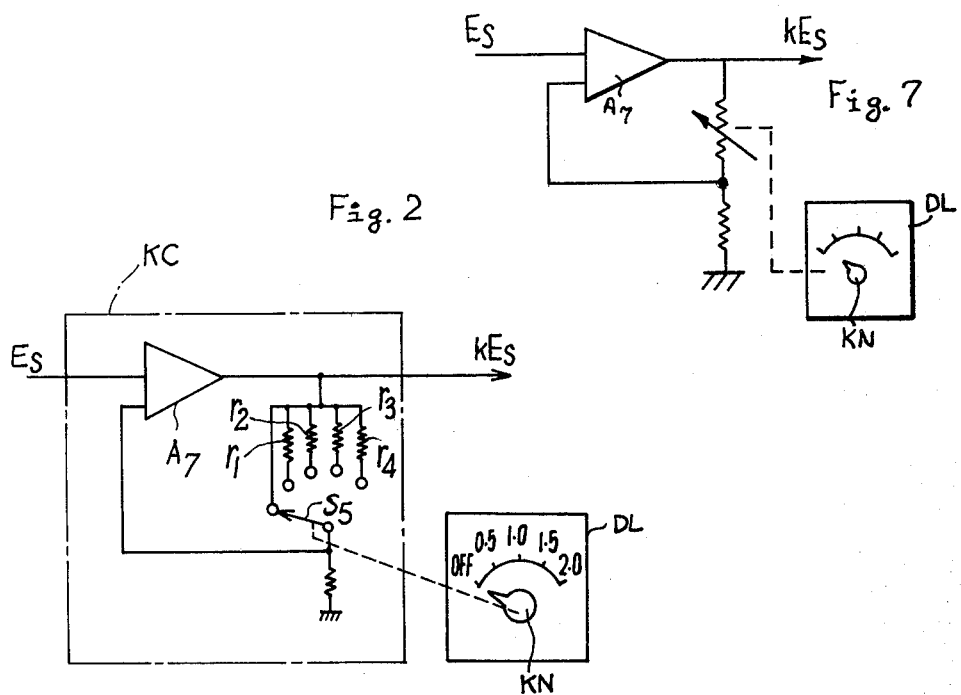
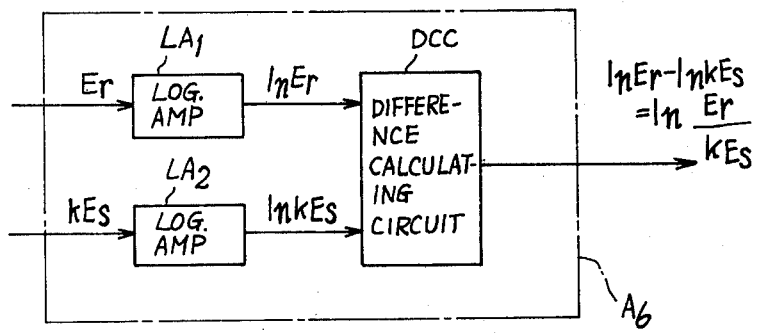

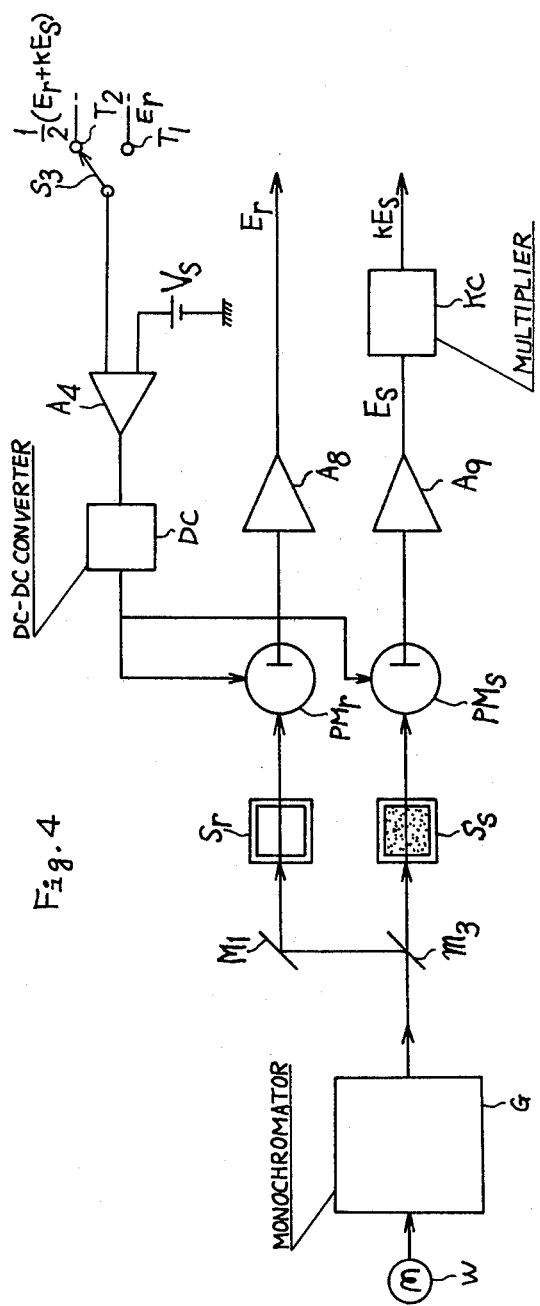

SPECTROPHOTOMETER

This invention relates to a spectrophotometer which is capable of measuring minute changes of the absorbance of a sample which has a relatively high absorbance, such as, for example, one with a high degree of stability.

As is well known, if the intensity of light incident on a sample is Io and the intensity of light transmitted through the sample is I, the absorbance of the sample is given as ln (Io/I). In the conventional spectrophotometers it has been customary to convert the quantities Io and I to corresponding electrical signals which are then converted to the logarithms thereof by means of a logarithmic converter.

In the logarithmic converter which utilizes the logarithmic characteristic of a semiconductor element, effort has been made to keep the performance of the measuring circuit stable by using transistors having equal temperature characteristics or resistors having temperature characteristics opposite to those of the transistors. However, the effort has not been successful and the conventional instruments are unstable with respect to temperature, so that the measured values as they are cannot be relied on.

Accordingly, the primary object of the invention is to provide a spectrophotometer which is stable, precise and accurate in measurement under varying conditions of the ambient temperature, and which is particularly suitable for measurement of samples having relatively high concentrations.

Another object of the invention is to provide a spectrophotometer which enables enlargement of minute changes of the absorbance of a sample at a relatively high level for clear indication and easy and accurate observation or recording.

Let the electrical signal corresponding to the previously mentioned intensity of incident light Io be Er; the electrical signal corresponding to the previously mentioned intensity of the transmitted light I be Es; $k$ be a constant; and $kEs \cong Er$, (i.e. kEs approximately equals Er), it is known that the following relation is obtained with a good approximation:

$$\log_{10}\left(\frac{Er}{Es}\right) \alpha \frac{Er - kEs}{Es + kEs}$$

In accordance with the invention, the measuring circuit of the spectrophotometer is controlled in such a manner that $Er + kEs = Vs$ (constant), so that without logarithmic conversion the absorbance of a sample can be obtained as a value proportional to $(Er - kEs)$, provided that the value Es is within a narrow range between $Er/k$ and $(Er/k) + \Delta$ (with $\Delta$ being a minute value), that is, $$Er/k \leqq Es \leqq (Er/k) + \Delta.$$

Let $kEs = Er + e$. Taking logarithms of both sides of this equation yields $$\ln kEs = \ln (Er + e),$$
therefore
$$\ln Es = \ln (Er + e) - \ln k.$$

If the value $e$ is small in comparison with Er, by approximation we obtain $$\ln Es = \ln Er + \frac{e}{Er} - \ln k.$$

$$\ln \left(\frac{Er}{Es}\right) = -\frac{e}{Er} + \ln k.$$

Since $e = kEs - Er$, the absorbance ln (Er/Es) of the sample is expressed as $$\ln \left(\frac{Er}{Es}\right) = \frac{Er - kEs}{Er} + \ln k.$$

On the other hand, $$Er = \frac{1}{2}(Er + Er) = \frac{1}{2}\{Er + (kEs - e)\} = \frac{1}{2}(Er + kEs).$$

Therefore, we obtain $$\ln \left(\frac{Er}{Es}\right) = \frac{2(Er - kEs)}{Er + kEs} + \ln k \quad (1)$$

The above relation applies in common logarithm with a different constant.

If the constant $k$ is set to such a value that the absorbance will be nearly equal to zero, that is, ln (Er/kEs) = 0, that is, if the value of $k$ is so selected that Er $\cong$ kEs, it is possible to measure the absorbance of a sample in a predetermined narrow range about the absorbance ln k obtained when $kEs = Er$ as a value proportional to the value (Er − kEs). By enlarging this value it is possible to measure minute changes of the absorbance.

The invention will be described further in detail with reference to the accompanying drawings, wherein like reference numerals and symbols in difference figures denote corresponding parts and wherein:

FIG. 2 is a detailed circuit diagram of a portion of FIG. 1;

FIG. 3 is a detailed circuit diagram of another portion of FIG. 1; and

FIGS. 4, 5, 6 and 7 are schematic showings of a portion of different embodiments of the invention.

Figure 1:
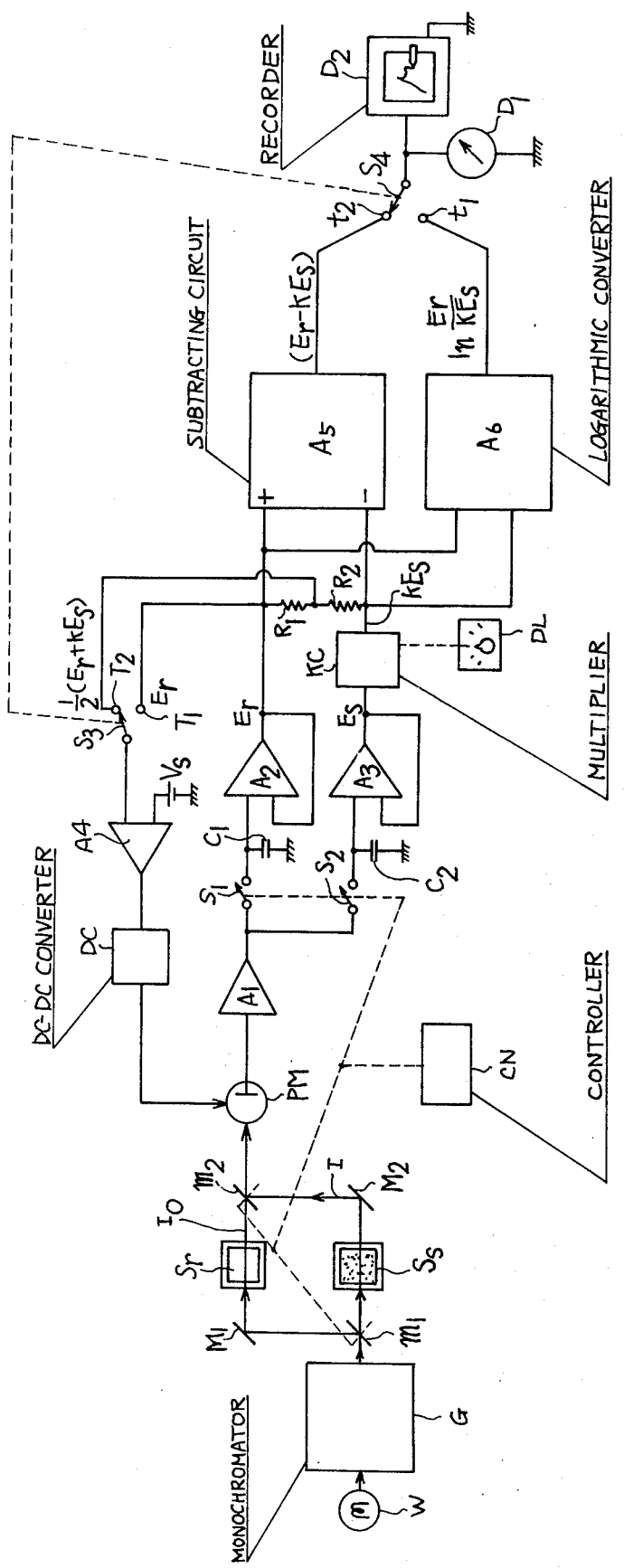
FIG. 1 is a schematic showing of one embodiment of the invention.

Now referring in detail to the drawings, first to FIG. 1, there is shown a source of light W, such as a tungsten lamp, the light from which enters a monochromator G including a suitable dispersing element (not shown) such as a grating. In the path of the monochromatic light emerging from the monochromator there is provided a beam splitter in the form of a first rotatable sector mirror ml. which splits the light from the monochromator into two beams. One of the two beams is passed through a cell Ss containing a sample material the absorbance of which is to be measured. The other beam is reflected by a plane mirror M1 and passed through a cell Sr containing a reference material such as solvent. The reference light beam Io transmitted through the solvent in the cell Sr advances toward a second rotatable sector mirror M2.

The light beam I transmitted through the sample in the cell Ss is reflected by a plane mirror M2 onto the second sector mirror m2. As the sector mirror m2 is rotated in ganged relation with the sector mirror m1, a photomultiplier tube PM receives the beams Io and I alternately so as to produce electrical signals corresponding to the intensities of the light beams Io and I, respectively.

The output signals from the photomultiplier PM are amplified by a pre-amplifier A1, to the output of which are connected in parallel a pair of sampling switches S1 and S2 which are ganged with the sector mirrors m1 and m2, with a suitable controller CN controlling the ganged operation of the switches S1, S2 and the sector mirrors m1, m2.

The ganged relation of the sector mirrors m1 and m2 and the sampling switches S1 and S2 is such that when the mirrors m1 and m2 cause the reference beam Io to be projected onto the photomultiplier tube PM, the switch S1 is closed so that the output from the photomultiplier tube PM (to be referred to as the reference output) is stored in a capacitor C1 while when the mirrors m1 and m2 cause the measuring beam I transmitted through the sample Ss to be received by the photomultiplier tube PM, the switch S2 is closed so that the output from the photomultiplier tube PM (to be referred to as the sample or measuring output) is stored in a capacitor C2.

The reference and measuring output signals stored in the capacitors C1 and C2 are amplified by buffer amplifiers A2 and A3 having a feedback circuit so as to appear as output signals Er and Es, respectively.

The output signal Es from the amplifiers A3 is applied to a multiplier KC which multiplies the input Es by the constant or factor $k$. This factor $k$ may be manually and selectively set at a dial DL to a desired one of predetermined different values the common logarithms of which are for example 0.5, 1.0, 1.5, 2.0.

The output Er from the amplifier A2 and the output kEs from the multiplier KC are applied to a subtracting circuit A5, which produces an output corresponding to the result of the subtraction (Er − kEs).

A mode-changing switch S3 has two fixed contacts T1 and T2. The output Er of the amplifier A2 is also applied directly to the contact T1 and also through a resistor R1 to the other contact T2, to which the output kEs is also applied simultaneously through a resistor R2 having the same resistance value as the resistor R1.

The switch S3 selectively applies the signal Er or (Er + kEs)/2 to one input of a dynode feedback error detecting amplifier A4, to the other input of which a constant voltage Vs is applied. The output of the amplifier A4 controls a high voltage generator such as a DC-DC converter DC, the output of which is applied to the photomultiplier tube PM. The feedback circuit comprising the switch S3, the constant voltage source Vs and the amplifier A4 is provided to regulate the sensitivity of the photomultiplier tube PM thereby to compensate for fluctuation of the energy level of the light source with different wavelengths, or fluctuation of the source voltage, etc.

The outputs of the amplifier A2 and the multiplier KC are also applied to a logarithmic converter A6, which produces an output corresponding to ln (Er/kEs). The output of the subtracting circuit A5 and the logarithmic converter A6 are applied through a switch S4 to an indicator D1 and a recorder D2.

In operation, the light from the source W is taken out through the monochromator G as a monochromatic light beam, which is split into two beams Io and I. The reference beam Io reflected by the mirror M1 and transmitted through the cell Sr is received by the photomultiplier tube PM while the other beam is transmitted through the sample cell Ss and is directed by the mirror M2 onto the photomultiplier tube as the measuring beam I.

The optical signals Io and I are converted to corresponding reference and sample electrical signals, which are amplified by the pre-amplifier A1 and then conducted through two separate parallel circuits so that the reference signal is stored in the capacitor C1 and then appears as the output Er of the buffer amplifier A2 while the sample signal is stored in the capacitor C2 and then appears as the output Es of the other buffer amplifier A3.

If the mode-changing switch S3 is in the real-line position as shown in FIG. 1, the dynode feedback circuit operates so that $Er + kEs = Vs$ (constant). Under the condition if the output (Er − kEs) of the subtracting circuit A5 is measured, it is possible to obtain a value proportional to the absorbance of the sample, as previously mentioned.

In actual measurement, first the arm of the switch S3 is brought into contact with the constant T1 to see the output of the logarithmic converter A6 on the indicator D1, with the arm of the switch 4 which is ganged with the switch S3 being in contact with a stationary contact t1. At this time, the measuring system operates in the same manner as that of the convertional absorption spectrophotometer. Then the dial DL is manually turned to set the constant $k$ to such a value that the output of the logarithmic converter A6 becomes less than 0.2, that is, $\log_{10}(Io/kI) \leq 0.2$. This range of 0 to 0.2 is obtained by calculation as a practical range within which the previously mentioned equation (1) applies.

Then the arm of the switch S3 is moved to the other contact T2. Since the system is so controlled by the dynode feedback circuit as to keep the value of Er + kEs constant as previously mentioned, by the output of the subtraction circuit A5 it is possible to obtain the value of $$\frac{Er - kEs}{Er + kEs}.$$

The calibrations of the dial DL for setting the factor or constant $k$ in the multiplier KC are given in $\log_{10} k$, so that if the output value of the circuit A5 and the set value of $k$ are added, the absorbance of the sample under measurement can be obtained by the previously mentioned equation (1).

FIG. 1 shows an example of the multiplier KC shown as a mere block in FIG. 1. The circuit KC comprises an amplifier A7 having a feedback circuit in which a plurality, say, four resistors r1, r2, r3 and r4 having different fixed resistance values are connected in parallel with each other, with a selector switch S5 the arm of which is moved by the knob KN of the dial DL so as to selectively connect one of the resistors r1 − r4 into the feedback circuit thereby to determine the gain of the amplifier A7, that is, the multiplication factor $k$.

In FIG. 2 the factor $k$ is changed stepwise. By using a variable resistor, such as in FIG. 7, instead of the fixed resistors r1 − r4 it is possible to change the gain continuously.

FIG. 3 shows an example of the logarithmic converter A6 shown in FIG. 1. The circuit comprises a pair of logarithmic amplifiers LA1 and LA2 to the inputs of which the signals Er and kEs are applied, respectively, and the outputs from which are applied to a difference calculating circuit DCC, which produces an output corresponding to the difference between the two inputs, that is, ln Er − ln kEs = ln (Er/kEs).

In FIG. 1, the rotating sector mirror m1 is used to split the monochromatic light into two beams. Instead of the sector mirror m1 a half mirror m3 may be used as shown in FIG. 4.

One half of the light from the monochromator passes through the half mirror m3 and then through the sample cell Ss to be received by a photomultiplier tube PMs, while the other half of the monochromatic light is reflected by the half mirror m3 and then the plane mirror M1 and then passed through the reference cell Sr to be received by a photomuliplier tube PMr. The outputs from the photomultiplier tubes PMr and PMs are amplified by amplifiers A8 and A9, respectively, to become the signals Er and Es, respectively. The signal Es are multiplied by the factor $k$ as in FIG. 1. The photomultiplier tubes PMr and PMs are simultaneously controlled by the output of the DC-DC converter.

The other component elements of the system of FIG. 4 which are not shown in FIG. 4 and the operation thereof are the same as in the system of FIG. 1, so that no further explanation will be given.

Figure 5:
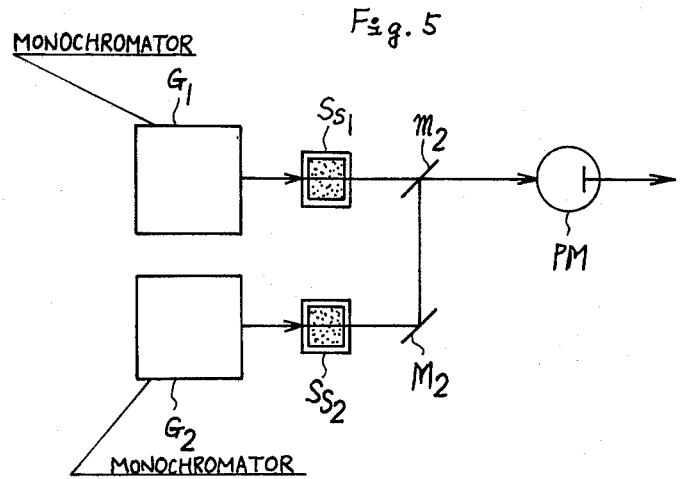
Figure 6:
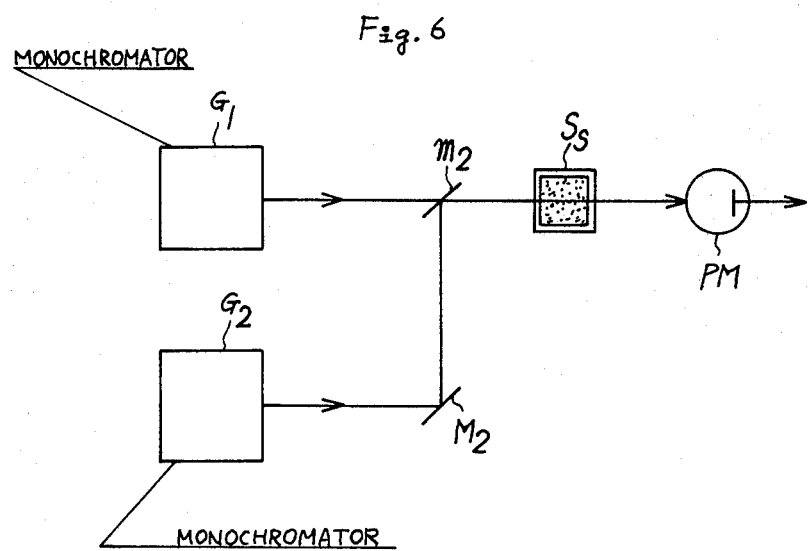

The principle of the invention can be applied to a dual-wavelength spectrophotometer as shown in FIGS. 5 and 6.

In FIG. 5 a monochromator G1 produces a monochromatic light beam of a wavelength λ1 which is transmitted through a sample cell Ss1, while another monochromator G2 produces a monochromatic light beam of a different wavelength λ2 which is transmitted through another sample cell Ss2 which contains the same sample as the cell Ss1.

The reference light beam λ1 transmitted through the cell Ss1 advances toward a rotating sector mirror m2, and the sample or measuring light beam λ2 transmitted through the cell Ss2 is reflected by a plane mirror M2 to advance toward the rotating sector mirror m2. The mirror m2 causes the beams λ1 and λ2 to be alternately projected to the photomultiplier tube PM, which produces corresponding electrical signal Er and Es alternately.

In FIG. 6 a single sample cell is provided between a rotating sector mirror m2 and a photomultiplier tube PM, so that the light beams of wavelengths λ1 and λ2 are alternately transmitted through the cell Ss to be received by the photomultiplier tube PM.

The electrical circuit connected to the output of the photomultiplier tube PM in both FIGS. 5 and 6 is substantially the same as in FIG. 1 so that no illustration or explanation will be required.

Thus, in accordance with the invention, in the circuit for measuring the value $$\frac{Er - kEs}{Er + kEs},$$

the temperature characteristics of the amplifiers A2, A3 and A4 can be made more stable than in the conventional logarithmic converter, so that even when the ambient temperature varies, the measured value is reliable. Since the absorbance can be accurately measured within a relatively narrow range, its minute changes can be accurately measured by enlarging them. Since no logarithmic converters except for the converter A6 are required, a relatively simple arrangement suffices for temperature compensation of the system, with resulting simplification of the circuit arrangement.

The logarithmic converter A6 is used only for coarse measurement of the absorbance, so that it can be a conventional logarithmic converter with an ordinary degree of temperatur compensation.

What we claim is:

1. A spectrophotometer comprising: means for providing a reference and a measuring monochromatic light beams; cell means; optical means for causing said beams to be transmitted through said cell means; first non-logarithmic electrical signal producing means for producing an electrical signal Er corresponding to said reference beam and an electrical signal Es corresponding to said measuring beam; non-logarithmic means for multiplying said electrical signal Es by a predetermined constant or factor $k$ to produce a signal corresponding to the value of kEs, said factor $k$ having a value such that ln (Er/kEs) approaches zero; second non-logarithmic electrical signal producing means for producing an electrical signal corresponding to the sum (Er + kEs); means for controlling said first electrical signal producing means so as to keep the value (Er + kEs) constant; and third non-logarithmic electrical signal producing means for producing an electrical signal corresponding to the difference (Er − kEs).

2. The spectrophotometer of claim 1, further including fourth electrical signal producing means for producing an electrical signal corresponding to ln (Er/kEs).

3. The spectrophotometer of claim 1, wherein said multiplying means includes means for changing said constant $k$.

4. The spectrophotometer of claim 3, wherein said constant changing means changes said constant $k$ stepwise.

5. The spectrophotometer of claim 3, wherein said constant changing means changes said constant $k$ continuously.

6. The spectrophotometer of claim 3, wherein said constant changing means includes means for indicating said constant $k$ in common logarithms.

7. The spectrophotometer of claim 1, further including means for indicating said electrical signal (Er − kEs).

8. The spectrophotometer of claim 2, further including means for selectively indicating said electrical signals (Er − kEs) and ln(Er/kEs).

9. The spectrophotometer of claim 2, wherein said fourth electrical signal producing means comprises a pair of logarithmic amplifiers to which said electrical signals Er and kEs are applied, respectively, and means for producing an electrical signal corresponding to the difference between the outputs of said logarithmic converters.

10. The spectrophotometer of claim 1, wherein said reference and measuring monochromatic light beams are of the same wavelength.

11. The spectrophotometer of claim 1, wherein said reference and measuring monochromatic light beams are of different wavelengths.

12. The spectrophotometer of claim 10, wherein said cell means comprises a reference cell and a sample cell, and said optical means causes said reference and measuring light beams to be transmitted through said reference and sample cells, respectively.

13. The spectrophotometer of claim 12, wherein said first electrical signal producing means includes a single photomultiplier tube, and said optical means causes said reference and measuring light beams to be alternately applied to said photomultiplier tube, said first electrical signal producing means further including first holding means for temporarily holding said electrical signal Er, second holding means for temporarily holding said electrical signal Es and switch means for applying said signals Er and Es to said first and second holding means, respectively.

14. The spectrophotometer of claim 12, wherein said first electrical signal producing means comprises a pair of photomultiplier tubes, and said optical means causes said reference light beam to be applied to one of said photomultiplier tubes and said measuring light beam to be applied to the other of said photomultiplier tubes.

15. The spectrophotometer of claim 11, wherein said cell means comprises a pair of cells adapted to contain the same kind of sample, and said optical means causes said reference light beam to be transmitted through one of said cells and said measuring light beam to be transmitted through the other of said cells.

16. The spectrophotometer of claim 11, wherein said cell means comprises a single sample cell, and said optical means causes said reference and measuring light beams to be alternately transmitted through said cell.

17. The spectrophotometer of claim 15, wherein said first electrical signal producing means includes a single photomultiplier tube, and said optical means causes said reference and measuring light beams transmitted through said cells to be alternately applied to said photomultiplier tube, said first electrical signal producing means further including first holding means for temporarily holding said electrical signal Er, second holding means for temporarily holding said electrical signal Es and switch means for applying said signal Er and Es to said first and second holding means, respectively.

18. The spectrophotometer of claim 16, wherein said first electrical signal producing means includes a single photomultiplier tube, and said optical means causes said reference and measuring light beams alternately transmitted through said single cell to be alternately applied to said photomultiplier tube, said first electrical signal producing means further including first holding means for temporarily holding said electrical signal Er, second holding means for temporarily holding said electrical signal Es and switch means for applying said signals Er and Es to said first and second holding means, respectively.

19. The spectrophotometer of claim 13, wherein said control means comprises feedback circuit means operable in response to the value of (Er + kEs) to control the dynode voltage of said photomultiplier tube.

20. The spectrophotometer of claim 14, wherein said control means comprises feedback circuit means operable in response to the value of (Er + kEs) to control the dynode voltages of said pair of photomultiplier tubes.

21. The spectrophotometer of claim 17, wherein said control means comprises feedback circuit means operable in response to the value of (Er + kEs) to control the dynode voltage of said single photomultiplier tube.

22. The spectrophotometer of claim 18, wherein said control means operable in response to the value of (Er + kEs) to control the dynode voltage of said single photomultiplier tube.

* * * * *